United States Patent [19]
Kuramochi et al.

[11] Patent Number: 5,661,111
[45] Date of Patent: Aug. 26, 1997

[54] METHOD FOR IMPROVING PLANT SALT-TOLERANCE

[75] Inventors: Hitoshi Kuramochi; Makoto Konnai, both of Tochigi; Tohru Tanaka; Yasushi Hotta, both of Saitama, all of Japan

[73] Assignees: Cosmo Research Institute; Cosmo Oil Co., Ltd., both of Tokyo, Japan

[21] Appl. No.: 561,702

[22] Filed: Nov. 22, 1995

[30] Foreign Application Priority Data

Nov. 28, 1994 [JP] Japan ................... 6-292492

[51] Int. Cl.⁶ ............... H01N 43/36; H01N 37/44; H01N 37/46
[52] U.S. Cl. ............... 504/284; 504/319; 504/320; 71/17
[58] Field of Search .................. 504/320, 284, 504/319; 71/17

*Primary Examiner*—Allen J. Robinson
*Assistant Examiner*—Brian G. Bembenick
*Attorney, Agent, or Firm*—Sughrue, Mion, Zinn, Macpeak & Seas

[57] ABSTRACT

A method for improving plant salt-tolerance is described, which comprises treating a plant with an active ingredient comprising at least one compound selected from the group consisting of 5-aminolevulinic acid, a derivative of 5-aminolevulinic acid, a salt of 5-aminolevulinic acid, a salt of derivatives of 5-aminolevulinic acid, and hemins. Furthermore, a salt-tolerant plant is described, wherein the plant is treated with the above-described active ingredient. Moreover, a method for causing recovery of a salt-damaged plant is described, comprising administering the above-described active ingredient to a salt-damaged plant.

14 Claims, No Drawings

METHOD FOR IMPROVING PLANT SALT-TOLERANCE

FIELD OF THE INVENTION

The present invention relates to a method for improving plant salt-tolerance (halotolerance, salinity-tolerance) to rear the plant even under high salt concentration conditions.

BACKGROUND OF THE INVENTION

Deserts and desert-like regions occupy ¼ to ⅓ of the terrestrial world and are expanding. Reasons for this desertification include using irrigation water with a high salt concentration, dams, irrigation and deficient draining equipment, and sea water reaching farm land, all causing salts such as NaCl, $Na_2SO_4$, $MgCl_2$, $CaCl_2$ and the like to accumulate in soil. In such salt-containing soil, almost all plants (excluding specific salt-tolerant plants) experience strongly restrained growth or lesions. According to Szabolcs (in the United Nations Desertification Prevention Congress at Nairobi, 1977), the soil accumulated with salts in the world had reached 952 million ha in 1977. To check enlargement of the deserts, afforestation and plant rearing have been attempted in the areas of the high-salt soil. However, because few plants can grow in the high-salt soil, the attempts to date are insufficient. Furthermore, because crop productivity in the high-salt soil is markedly low, little of the high-salt land is used as farmland.

In the Middle East, salt water processed into fresh water is used for agricultural irrigation. However, because enormous processing of salt water into fresh water requires much energy and much expense, and has much environmental impact, obtaining large quantities of irrigation water with a low salt concentration at low cost has been very difficult.

Moreover, in advanced nations, fertilization causes salt accumulation with corresponding problems such as deteriorated crop yield.

Some aspects of selection and rearing of salt-tolerant plants have been studied. For example, a salt-tolerant variety of rice is known. Furthermore, breeding salt-tolerant plants by adapting a callus of a plant to a high salt medium and reproducing the plant has been attempted. Moreover, a search for a gene related to salt-tolerance and a recombination of the gene has been studied to improve plant salt-tolerance.

On the other hand, there have been few studies directed to developing an agent for improving salt-tolerance. Only use of gibberellin ($GA_3$) has been reported. (Zhao Ke-fu et al., *Aust. J. Plant Physiol.*, vol. 13, pp. 547–551 (1986)).

However, in these above-mentioned earlier methods for improving plant salt-tolerance, the salt-tolerance obtained by a selection or bleeding is insufficient, and what characteristic of plants relates to salt-tolerance was unknown.

In addition, in the study of plant callus, the desired plant could not be obtained, and in the gene recombination, the gene related to salt-tolerance was not specified. Further, in developing an agent for improving salt-tolerance, prior to the invention of this application, others only knew merely that gibberellin slightly relieves salt stress.

On the other hand, 5-aminolevulinic acid and salts thereof are useful as a herbicide (U.S. Pat. No. 5,127,938), an insecticide (EP-A-326835), to accelerate plant growth (U.S. Pat. No. 5,298,482) and an agent for improving the pigmentation of apple rinds (U.S. Pat. No. 5,318,788). Parts of esters of 5-aminolevulinic acids and N-acyl-5-aminolevulinic acids are useful as a herbicide (JP-A-4-9360; the term "JP-A" as used herein means an unexamined published Japanese patent application). However, it was not known previously that 5-aminolevulinic acid and derivatives thereof improve plant salt-tolerance.

Developing an effective method for improving plant salt-tolerance would prevent the desertification of arable land and would allow crop production in high-salt soil. Correspondingly, an important food problem associated with ever increasing population would be solved or alleviated. Furthermore, an effective method of achieving plant salt-tolerance would have many other benefits, such as improving salt-to-fresh water distillation for irrigation water and reducing the amount of irrigation water needed.

SUMMARY OF THE INVENTION

An object of the present invention is to provide a method for improving plant salt-tolerance to enable plant growth in soil having a high salt concentration.

Various compounds have been investigated with the object of improving plant salt-tolerance. As a result, the present inventors found that compounds selected from 5-aminolevulinic acid (hereinafter referred to as "5-ALA") known as an accelerator for plant growth, derivatives thereof, salts thereof, and hemins provide the desired effect.

This and other objects of the present invention have been attained by a method for improving plant salt-tolerance, which comprises treating the plant with an active ingredient comprising at least one compound selected from the group consisting of 5-ALA, derivatives thereof, salts thereof (i.e., salts of 5-ALA and salts of 5-ALA derivatives), and hemins.

Furthermore, this and other objects of the present invention have been attained by a salt-tolerant plant, wherein the plant is treated with an active ingredient comprising at least one compound selected from the group consisting of 5-aminolevulinic acid, a derivative of 5-aminolevulinic acid, a salt of 5-aminolevulinic acid, a salt of derivatives of 5-aminolevulinic acid, and hemins, and has salt-tolerance.

Moreover, this and other objects of the present invention have been attained by a method for causing recovery of a salt-damaged plant, which comprises administering to a salt-damaged plant an active ingredient comprising at least one compound selected from the group consisting of 5-aminolevulinic acid, a derivative of 5-aminolevulinic acid, a salt of 5-aminolevulinic acid, a salt of derivatives of 5-aminolevulinic acid, and hemins.

DETAILED DESCRIPTION OF THE INVENTION

In the method for improving plant salt-tolerance according to the present invention, examples of the salts of 5-ALA (5-aminolevulinates) and the salts of derivatives of 5-ALA used as the active ingredient include acid addition salts such as hydrochloride, phosphate, nitrate, sulfate, acetate, propionate, butyrate, valerate, citrate, fumarate, maleate, and malate; and metal salts such as sodium salt, potassium salt and calcium salt. These salts are used as an aqueous solution, and the effects thereof are the same as those of 5-ALA.

5-ALA and the salts thereof are known, and they can be produced by any known method such as chemical synthesis, microbial production and enzymatic production. When they are produced by the microbial or enzymatic production, the products obtained can be used as the active ingredient of the present invention without separation and purification steps as long as the products obtained contain no substance harmful to a plant.

Examples of the derivatives of 5-ALA include esters of 5-ALA (5-aminolevulinates) and N-acyl-5-aminolevulinic acids.

Examples of the esters of 5-ALA include alkyl esters of 5-ALA, in which the alkyl moiety is a straight-chain, branched or cyclic alkyl group having 1 to 24 carbon atoms which may have one or more substituents such as a hydroxyl group, alkoxy group, and phenyl group. Preferable examples of the group forming an ester with 5-ALA include a methyl group, ethyl group, isopropyl group, n-hexyl group, cyclohexyl group, n-heptyl group, n-octyl group, n-nonyl group, n-dodecyl group, n-hexadecyl group, benzyl group, phenethyl group, 3-phenylpropyl group, hydroxyethyl group, and ethoxyethyl group.

Examples of the N-acyl-5-aminolevulinic acids include compounds obtained by acylating 5-ALA at its amino group with an acyl group such as an alkanoyl group having 1 to 24 carbon atoms, an aromatic acyl group having 7 to 24 carbon atoms, or a benzyloxycarbonyl group having 8 to 24 carbon atoms. Preferable examples of the acyl group in the N-acyl-aminolevulinic acids include an acetyl group, n-pentanoyl group, n-hexanoyl group, n-nonanoyl group, benzoyl group and benzyloxycarbonyl group.

These above-mentioned esters of 5-ALA and N-acyl-5-aminolevulinic acids can be made by any known chemical synthesis method as disclosed in JP-A-4-9360. The products of such a method can be used as the active ingredient of the present invention without separation and purification steps as long as they contain no substance harmful to a plant.

The derivatives of 5-ALA may be used in the form of a salt, and examples of the salt include those enumerated above as the salts of 5-ALA such as acid addition salts and metal salts.

Examples of the hemins used as the active ingredient of the present invention include tetrapyrrole compounds containing iron (compounds having a porphyrin ring containing iron). Specific examples thereof include heme (haem), hemin, and hematin. Furthermore, they include compounds containing the hemins in the structure such as coordination compounds (e.g., hemochrome) and protein complexes (e.g., hemoglobin). Additionally, they include natural materials containing the hemins such as blood powder (prepared by butchering livestock and drying the blood obtained). They can be used as the active ingredient of the present invention without separation and purification steps as long as they have no substance harmful to a plant.

In the method for improving plant salt-tolerance of the present invention, 5-ALA, derivatives thereof, salts thereof and hemins are used alone or in combination of two or more thereof as an active ingredient. The composition for improving the salt-tolerance may be prepared by using only these above-mentioned compounds, or by mixing therewith other compounds such as agents for regulating plant growth, saccharides, amino acids, organic acids, alcohols, vitamins and minerals.

Examples of the agents for regulating plant growth include brassinolide (e.g., epibrassinolide), choline (e.g., choline chloride, choline nitrate), indolebutyric acid, indoleacetic acid, ethychlozate, 1-naphthylacetamide, isoprothiolane, nicotinic-acid amide, hydroxyisoxazole, calcium peroxide, benzylaminopurine, methasulfocarb, oxyethylene docosanol, ethephon, cloxyfonac, gibberellin, streptomycin, daminozide, 4-CPA, ancymidol, inabenfide, uniconazole, chlormequat, dikegulac, mefluidide, calcium carbonate and piperonyl butoxide.

Examples of the saccharides include glucose, sucrose, xylitol, sorbitol, galactose, xylose, mannose, arabinose, madulose, ribose, rhamnose, fructose, maltose, lactose and maltotriose.

Examples of the amino acids include asparagine, glutamine, histidine, tyrosine, glycine, arginine, alanine, tryptophan, methionine, valine, proline, leucine, lysine and isoleucine.

Examples of the organic acids include formic, acetic, propionic, butyric, valeric, oxalic, phthalic, benzoic, lactic, citric, tartaric, malonic, malic, succinic, glycolic, glutamic, aspattic, maleic, caproic, caprylic, myristic, stearic, palmitic, pyruvic and α-ketoglutaric acids.

Examples of the alcohols include methanol, ethanol, propanol, butanol, pentanol, hexanol and glycerol.

Examples of the vitamins include nicotinic-acid amide, vitamin $B_6$, vitamin $B_{12}$, vitamin $B_5$, vitamin C, vitamin $B_{13}$, vitamin $B_1$, vitamin $B_3$, vitamin $B_2$, vitamin $K_3$, vitamin A, vitamin $D_2$, vitamin $D_3$, vitamin $K_1$, α-tocopherol, β-tocopherol, γ-tocopherol, δ-tocopherol, p-hydroxybenzoic acid, biotin, folic acid, nicotinic acid, pantothenic acid, and α-liponic acid.

Examples of the minerals include nitrogen, phosphoric acid, potassium, boron, manganese, zinc, copper, iron, molybdenum, and magnesium oxide.

The composition for use in the method of the present invention may be in any form generally used for such applications, such as wettable powders, flowables, powders, particles, granules and liquid. These composition forms may be prepared by a conventional method by using additives such as solvents, dispersants and extenders.

In addition, the composition for use in the method of the present invention may contain agriculturally and horticulturally acceptable carriers.

Next, details of the method for improving plant salt-tolerance according to the present invention will be explained below.

According to the method of the present invention, plants can be cultivated in a high salt concentration. "High salt concentration" means a condition in which a salt damages a plant. Soil having high salt concentration may be called "high salinity" or "high salt" soil. The salt concentration thereof is not particularly limited; however, generally associated with the high salinity, the electric conductivity of the soil solution (dry soil weight: water weight=1:5) is at least 0.5 mmho/cm (milimho/cm), preferably at least 1.0 mmho/cm, and more preferably at least 2.0 mmho/cm. The unit "mho/cm" means a specific electric conductivity of a solution. The conductivity is represented by a reciprocal of electric resistance between two polar plates measured with an electric conductivity meter when the two polar plates of one $cm^2$ are placed at an interval of one cm.

In irrigation water, the method of the present invention is effective for irrigation water having a salt concentration of at least 300 ppm in water.

The above-described salt concentration is varied depending on plant varieties, soil properties, temperature, humidity, water content in soil, cultivating conditions, salt-tolerance originally associated with a plant, and other like factors.

For example, when plants having high salt-tolerance such as barley and wheat are cultivated, the soil used preferably has an electric conductivity of 3.0 to 30 mmho/cm according to the above-described electric conductivity, and the irrigation water used preferably has a salt concentration of 5,000 ppm to 30,000 ppm.

In the method of the present invention for improving salt-tolerance, treating a plant with the active ingredient may be accomplished any method as long as the plant can absorb the active ingredient. Examples of application methods include spraying foliage with the active ingredient, spraying soil with the active ingredient, and a hydroponic treatment in which the active ingredient is absorbed in roots after dissolving or suspending it to a medium such as water. Furthermore, the active ingredient may be absorbed before potting or cutting a plant.

For the above-mentioned foliage treatment, the concentration of the active ingredient is preferably adjusted to 1 µmol/l to 15 mmol/l, more preferably 5 µmol/l to 10 mmol/l, and the thus prepared active ingredient is preferably applied in an amount of one to 1,000 l, more preferably 10 to 300 l, per 10 ares of ground. In applying the active ingredient to a plant as to which the active ingredient adheres to the foliage with difficulty, a wetting agent preferably is used. The kind and the amount of the wetting agent is not particularly limited, and any of the wetting agents generally used may be added.

In carrying out the above-mentioned the hydroponic treatment, the active ingredient is preferably applied to a plant at a concentration of 6 nmol/l to 300 µmol/l, more preferably 60 nmol/l to 130 µmol/l. When the active ingredient is absorbed before potting or cutting a plant, the concentration of the active ingredient is preferably adjusted to the same range of the above-described hydroponic treatment. The soaking time for this absorption is preferably for at least one hour, more preferably at least 6 hours. Preferably, if the soaking time is short, a high concentration is selected from the above-described concentration range; and if the soaking time is long, a low concentration is selected from the above-described concentration range.

When carrying out the soil treatment, the active ingredient preferably is applied in an amount of 3 mmol to 5 mol, more preferably 6 mmol to 2 mol, per 10 ares of ground. The method of the soil treatment is not particularly limited. For example, the active ingredient may be directly plowed into the soil or irrigated in solution form. Moreover, the active ingredient may be dipped as a hydroponic treatment in a low concentration selected from the above-described concentration range.

To obtain the effects of active ingredient according to the present invention, any of the above-described treatments may be adopted, and the treatment may be carried out at any stage of growth of a plant. One treatment may be sufficient to obtain the desired salt-tolerant effects. However, carrying out the treatment several times can further heighten the advantageous effects. When the treatment for improving plant salt-tolerance is carried out several times, other treatments may be performed in combination therewith. Furthermore, other agricultural chemicals and fertilizer may be used in combination with the method of the present invention, as long as the effects of the active ingredient according to the present invention are not lowered.

In cultivating a plant using the method according to the present invention in high salinity soil, the soil preferably is treated with the method according to the present invention to prevent salt damage before or while the plant is potted. Furthermore, when symptoms of salt damage to a plant are observed, the plant may be treated with the method according to the present invention to cause recovery of the damaged plant.

Plants to which the method according to the present invention is applied are not particularly limited. The method according to the present invention is applied to plants which are widely cultivated in agricultural and horticultural fields.

Plant salt-tolerance can be improved by treating plants according to the method of the present invention. However, because the salt-tolerance provided by the present inventive method relates to the salt-tolerance originally associated with the plant, it is preferred that plants having high salt-tolerance originally are treated using a method according to the present invention. Examples of plants having high salt-tolerance include cotton, asparagus, barley, wheat, corn, beet, tomato, fig, date palm, and grass such as salt grass and Bermuda grass.

Furthermore, plants originally having low salt-tolerance suffer damage from even a slight amount of salts. Improving the salt-tolerance of such plants with low salt-tolerant is very significant in agricultural and horticultural fields. Examples of such plants include radish, cabbage, Chinese cabbage, cucumber, eggplant, melon, rice, soybean, red clover, safflower, and sunflower.

The mechanism of plant salt-tolerance has been studied, and various explanations such as opening and closing of stomata, accumulation of prolines and betaines, and revelation of salt-tolerant protein have been given. However, there has been no fixed theory. (Tetsuko Takabe, *Japanese Science And Technology*, vol. 34, No. 268, pp. 48–53 (1993)). In addition, knowledge has been lacking about the relationship between proposed salt-tolerance mechanisms and the compounds functioning as the active ingredient in the method according to the present invention.

The method according to the present invention improves plant salt-tolerance effectively and simply. Furthermore, the method according to the present invention improves crop productivity in high salinity conditions using, for example, high-salt soil or irrigation water having high salinity.

The present invention is now illustrated in greater detail by way of the following examples, but it should be understood that the present invention is not to be construed as being limited thereto. Unless otherwise indicated herein, all parts, percents, ratios and the like are by weight.

EXAMPLES

Example 1 and Comparative Examples 1–11

A porcelain pot (inner diameter: 12 cm) having no drainage hole was filled with 600 g of soil of cultivated land. Seven to eight grains of cotton seeds (variety: M-5 Acala) were sowed thereon, covered with one cm of soil, and allowed to grow in a greenhouse. The cotton was cultivated in a usual manner, and then, when the seed leaves developed, the foliage was spray-treated with compositions for improving salt-tolerance containing a sample compound having a concentration shown in Table 1 and an extender (0.05% v/v; Neoesterin, produced by Kumiai Chemical Industry Co., Ltd.) in an amount of 100 l per 10 ares. The optical concentrations of the sample compounds were each selected based on the generally used concentrations thereof. After 4 days of the treatment, sodium chloride corresponding to 0%, 0.5%, 0.75%, 1% or 1.5% by weight per the soil weight as shown in Table 1 was dissolved in 30 ml of water, and then the solution obtained was dropwise added to the soil.

After the usual cultivation was continued, visual observation was performed on the 23rd day after the treatment. The results of salt damage were ranked according to the following scale:

0: no salt damage
1: slight salt damage
2: low salt damage
3: apparent salt damage
4: high salt damage
5: plant died due to salt damage The results obtained are shown in Table 1.

TABLE 1

| | Sample compound | (Concentration (ppm)) | 0 | 0.5 | 0.75 | 1 | 1.5 |
|---|---|---|---|---|---|---|---|
| | Untreated | | 0 | 1 | 2 | 3 | 5 |
| Example 1 | 5-ALA hydrochloride | (10) | 0 | 1 | 2 | 4 | 4 to 5 |
| | | (30) | 0 | 1 | 1 | 1 to 2 | 3 |
| | | (100) | 0 | 0 | 0 to 1 | 1 | 2 |
| | | (300) | 0 | 0 | 0 | 0 to 1 | 1 to 2 |
| Comparative Example 1 | Benzyladenine | (0.1) | 0 | 1 | 2 | 3 | 5 |
| | | (0.3) | 0 | 1 | 2 | 3 | 5 |
| | | (1) | 0 | 1 | 4 | 4 | 5 |
| | | (3) | 0 | 1 | 4 | 5 | 5 |
| Comparative Example 2 | Ancymidol | (0.5) | 0 | 1 | 2 | 4 | 5 |
| | | (1) | 0 | 1 | 3 | 4 | 5 |
| | | (3) | 0 | 1 | 2 | 4 to 5 | 5 |
| | | (10) | 0 | 1 | 2 | 4 to 5 | 5 |
| Comparative Example 3 | Paclobutrazol | (0.1) | 0 | 1 | 3 | 4 | 5 |
| | | (0.3) | 0 | 1 | 3 | 4 | 5 |
| | | (1) | 0 | 1 | 2 | 4 | 5 |
| | | (3) | 0 | 1 | 2 | 4 | 5 |
| Comparative Example 4 | Maleic acid hydrazide cholinate | (0.3) | 0 | 1 | 2 | 4 | 5 |
| | | (1) | 0 | 1 | 2 | 4 | 5 |
| | | (3) | 0 | 1 | 2 | 4 | 5 |
| | | (10) | 0 | 1 | 2 | 4 | 5 |
| Comparative Example 5 | Indolebutyric acid | (0.1) | 0 | 1 | 2 | 4 | 5 |
| | | (0.3) | 0 | 1 | 2 | 4 to 5 | 5 |
| | | (1) | 0 | 1 | 3 | 4 to 5 | 5 |
| | | (3) | 0 | 1 to 2 | 3 | 4 | 5 |
| Comparative Example 6 | Hydroxyisoxazole | (0.3) | 0 | 1 | 2 | 4 | 5 |
| | | (1) | 0 | 1 to 2 | 2 | 4 to 5 | 5 |
| | | (3) | 0 | 1 to 2 | 2 | 4 to 5 | 5 |
| | | (10) | 0 | 1 | 2 | 4 to 5 | 5 |
| Comparative Example 7 | Esrel | (0.3) | 0 | 1 | 2 | 4 | 5 |
| | | (1) | 0 | 1 | 4 | 4 | 5 |
| | | (3) | 0 | 1 | 2 | 5 | 5 |
| | | (10) | 0 | 1 to 2 | 2 | 4 | 5 |
| Comparative Example 8 | Gibberellin (GA$_3$) | (0.03) | 0 | 1 | 2 | 4 | 5 |
| | | (0.1) | 0 | 1 | 2 | 4 to 5 | 5 |
| | | (0.3) | 0 | 1 | 2 | 4 to 5 | 5 |
| | | (1) | 0 | 1 | 2 | 4 | 5 |
| Comparative Example 9 | Indoleacetic acid | (0.3) | 0 | 1 | 2 | 4 | 5 |
| | | (1) | 0 | 1 to 2 | 2 | 4 | 5 |
| | | (3) | 0 | 1 | 3 | 4 | 5 |
| | | (10) | 0 | 1 | 3 | 4 to 5 | 5 |
| Comparative Example 10 | Abscisic acid | (1) | 0 | 1 | 2 | 5 | 5 |
| | | (3) | 0 | 1 to 2 | 3 | 4 to 5 | 5 |
| | | (10) | 0 | 1 to 2 | 3 | 4 to 5 | 5 |
| | | (30) | 0 | 1 to 2 | 3 | 4 to 5 | 5 |
| Comparative Example 11 | N-Dimethylaminosuccineamide (B-9) | (0.3) | 0 | 1 | 2 | 4 to 5 | 5 |
| | | (1) | 0 | 1 | 2 | 4 | 5 |
| | | (3) | 0 | 1 | 2 | 4 to 5 | 5 |
| | | (10) | 0 | 1 | 2 | 4 | 5 |
| | | (100) | 0 | 1 | 2 | 4 | 5 |

The results in Table 1 show that the cotton treated with the 5-ALA hydrochloride has remarkably improved salt-tolerance. Furthermore, the data relating to the Comparative Examples show that applying compounds known as a phytohormone or a plant growth regulator alone does not improve the salt-tolerance of the cotton or allows salt to damage cotton.

Example 2

A plastic vessel (30 cm by 40 cm, height: 15 cm) having no drainage hole was filled with 6,000 g of soil from cultivated land. Seeds of cotton (variety: M-5 Acala), safflower, soy beans, sunflower or corn were sowed thereon, covered with one cm of the soil, and allowed to rear in a greenhouse. These plants were cultivated in a usual manner, and then, when the length thereof over the ground was about 5 cm, (October 9th), the foliage was spray-treated with a composition for improving salt-tolerance containing a 5-ALA hydrochloride having a concentration shown in Table 2 and an extender (0.05% v/v; Neoesterin, produced by Kumiai Chemical Industry Co., Ltd.) in an amount of 100 l per 10 ares. After three days of the treatment (October 12th), sodium chloride (NaCl) corresponding to 0%, 1% or 2% by weight per the soil weight as shown in Table 2 was dissolved in 500 ml of water, and then the solution obtained was dropwise added to the soil.

After continuing the usual cultivation, visual observation was made on December 1st. The results were evaluated in the same manner as in Example 1. The results obtained are shown in Table 2 below using the same grading scale as in Example 1.

TABLE 2

| Amount added of NaCl per weight of soil (% by weight) | Plant variety | 5-ALA hydrochloride (concentration (ppm)) | | | |
|---|---|---|---|---|---|
| | | 0 | 100 | 300 | 500 |
| 0 | Corn | 0 | 0 | 0 | 0 |
| | Sunflower | 0 | 0 | 0 | 0 |
| | Soy beans | 0 | 0 | 0 | 0 |
| | Cotton | 0 | 0 | 0 | 0 |
| | Safflower | 0 | 0 | 0 | 0 |
| 1 | Corn | 4 | 3 | 2 | 1 |
| | Sunflower | 5 | 5 | 4 | 3 |
| | Soy beans | 5 | 5 | 3 | 3 |
| | Cotton | 4 | 1 | 0 | 0 |
| | Safflower | 5 | 5 | 4 | 4 |
| 2 | Corn | 5 | 5 | 4 | 3 |
| | Sunflower | 5 | 5 | 5 | 4 |
| | Soy beans | 5 | 5 | 5 | 4 |
| | Cotton | 5 | 2 | 1 | 1 |
| | Safflower | 5 | 5 | 5 | 5 |

The results shown in Table 2 show that salt-tolerance of plants of various varieties is improved by the treatment with the 5-ALA hydrochloride. Cotton having high salt-tolerance which is treated with the 5-ALA hydrochloride can grow almost normally without being damaged even on a salt concentration as high as 2%.

Example 3

A plastic vessel (30 cm by 40 cm, height: 15 cm) having no drainage hole was filled with 6,000 g of soil of cultivated land. Asparagus seeds were sowed thereon, covered with one cm of the soil, and allowed to grow in a greenhouse. The asparagus was cultivated in a usual manner, and then, when the length thereof over the ground was about 5 cm (October 18th), the foliage was spray-treated with a composition for improving salt-tolerance containing 300 ppm of a 5-ALA hydrochloride and 0.05% (v/v) of an extender (Neoesterin, produced by Kumiai Chemical Industry Co., Ltd.) in an amount of 100 l per 10 ares. After 4 days of the treatment (October 22th), sodium chloride corresponding to 1.5% by weight per the soil weight was dissolved in 500 ml of water, and then the solution obtained was dropwise added to the soil.

After continuing the usual cultivation, visual observation was made on December 1st. The results are reported in terms of a ratio of the number of the plants died from and/or yellowed by salt damage to the number of the plants which were untreated with the 5-ALA hydrochloride. The results obtained are shown in Table 3.

TABLE 3

| 5-ALA hydrochloride | Normal (%) | Yellowed (%) | Dead (%) |
|---|---|---|---|
| Treated | 92 | 6 | 2 |
| Untreated | 8 | 56 | 36 |

The results in Table 3 show that the salt-tolerance of asparagus is also improved by the treatment with the 5-ALA hydrochloride. As shown in this Example, although the salt-tolerance is slightly different between individual plants, the overall effect of the present invention is a great effect improving the salt-tolerance of any individual plant.

Example 4

Young cotton plants were prepared in the same manner as in Example 1 (young plants at a seed leaf development stage and those at a first leaf development stage were prepared). The foliage thereof was spray-treated with a composition containing a sample compound of a concentration shown in Table 4 and an extender (0.5% v/v; Neoesterin, produced by Kumiai Chemical Industry Co., Ltd.) in an amount of 100 l per 10 ares on February 21st. However, since 5-ALA-n-nonanoicamide and hemin had low water solubility, they were applied in the form of a wettable powder. Further, N-acyl-5-ALA and esters of 5-ALA were used as hydrochloride. After 5 days of the treatment (February 26th), sodium chloride corresponding to 1% by weight per the soil weight was dissolved in 30 ml of water, and then the solution was dropwise added to the soil.

After the usual cultivation, visual observation was done on March 25th. The results were evaluated in the same manner as in Example 1. The results obtained are shown in Table 4 below.

TABLE 4

| Sample compound | (Concentration (ppm)) | Seed leaf development | First leaf development |
|---|---|---|---|
| Untreated | | 4 | 5 |
| 5-ALA ethyl ester | (100) | 3 | 3 |
| | (500) | 3 | 4 |
| 5-ALA hexyl ester | (100) | 2 | 2 |
| | (500) | 3 | 3 |
| 5-ALA heptyl ester | (100) | 2 | 3 |
| | (500) | 2 | 2 |
| 5-ALA octyl ester | (100) | 2 | 2 |
| | (500) | 2 | 3 |
| 5-ALA nonyl ester | (100) | 3 | 5 |
| | (500) | 4 | 4 |
| 5-ALA dodecyl ester | (100) | 2 | 3 |
| | (500) | 2 | 3 |
| 5-ALA hexadecyl ester | (100) | 2 | 3 |
| | (500) | 2 | 3 |
| 5-ALA isopropyl ester | (100) | 2 | 1 |
| | (500) | 2 | 3 |
| 5-ALA cyclohexyl ester | (100) | 2 | 3 |
| | (500) | 2 | 3 |
| 5-ALA benzyl ester | (100) | 3 | 3 |
| | (500) | 3 | 3 |
| 5-ALA phenethyl ester | (100) | 2 | 2 |
| | (500) | 3 | 3 |
| 5-ALA-3-phenyl propyl ester | (100) | 3 | 3 |
| | (500) | 2 | 3 |
| 5-ALA ethoxy ethyl ester | (100) | 3 | 4 |
| | (500) | 3 | 5 |
| 5-ALA-n-hexanoicamide | (100) | 3 | 3 |
| | (500) | 3 | 3 |
| 5-ALA-n-nonanoicamide | (100) | 2 | 2 |
| | (500) | 3 | 2 |
| Hemin | (100) | 2 | 2 |
| | (500) | 2 | 2 |
| 5-ALA hydrochloride | (100) | 2 | 2 |
| | (500) | 2 | 1 |

The results in Table 4 show that 5-ALA, esters of 5-ALA, N-acyl-5-aminolevulinic acids and hemin can improve plant salt-tolerance.

Example 5

Young cotton plants were prepared in the same manner as in Example 1 (young plants at a first leaf development stage were prepared). The foliage thereof was spray-treated with a composition containing a sample compound of a concentration shown in Table 5 and an extender (0.05% v/v; Neoesterin, produced by Kumiai Chemical Industry Co., Ltd.) in an amount of 100 l per 10 ares on June 15th. However, because 5-ALA-n-nonanoicamide and hemin had low water-solubility, they were applied in the form of a wettable powder. Further, amides and esters of 5-ALA amide were used in hydrochloride form. After 4 days of the treatment (June 19th), sodium halide corresponding to 0%, 1.0%, 1.25% or 1.5% by weight per the soil weight was dissolved in 30 ml of water, and then the solution obtained was dropwise added to the soil.

After the usual cultivation, visual observation was done on July 2nd. The results were evaluated by a relative value of 0% to 100% according to salt damage. The experiment was performed twice to obtain an average of the relative values. The results are shown in Table 5 below.

TABLE 5

| Sample compound | (Concentration (ppm)) | Amount added of NaCl per weight of soil (% by weight) | | | |
|---|---|---|---|---|---|
| | | 0 | 1.0 | 1.25 | 1.5 |
| Untreated | | 0 | 45 | 75 | 100 |
| 5-ALA ethyl ester | (100) | 0 | 20 | 75 | 100 |
| | (500) | 0 | 30 | 75 | 85 |
| 5-ALA hexyl ester | (100) | 0 | 35 | 45 | 95 |
| | (500) | 0 | 40 | 50 | 95 |
| 5-ALA heptyl ester | (100) | 0 | 40 | 70 | 100 |
| | (500) | 0 | 30 | 60 | 75 |
| 5-ALA octyl ester | (100) | 0 | 30 | 80 | 80 |
| | (500) | 0 | 45 | 80 | 100 |
| 5-ALA nonyl ester | (100) | 0 | 45 | 75 | 95 |
| | (500) | 0 | 25 | 50 | 95 |
| 5-ALA dodecyl ester | (100) | 0 | 40 | 70 | 85 |
| | (500) | 0 | 45 | 75 | 100 |
| 5-ALA hexadecyl ester | (100) | 0 | 40 | 50 | 85 |
| | (500) | 0 | 40 | 70 | 95 |
| 5-ALA isopropyl ester | (100) | 0 | 35 | 50 | 90 |
| | (500) | 0 | 40 | 70 | 85 |
| 5-ALA cyclohexyl ester | (100) | 0 | 30 | 75 | 90 |
| | (500) | 0 | 35 | 75 | 85 |
| 5-ALA benzyl ester | (100) | 0 | 25 | 75 | 75 |
| | (500) | 0 | 45 | 75 | 100 |
| 5-ALA phenethyl ester | (100) | 0 | 40 | 70 | 95 |
| | (500) | 0 | 30 | 75 | 95 |
| 5-ALA-3-phenyl propyl ester | (100) | 0 | 35 | 75 | 85 |
| | (500) | 0 | 45 | 75 | 100 |
| 5-ALA ethoxy ethyl ester | (100) | 0 | 40 | 75 | 95 |
| | (500) | 0 | 40 | 75 | 90 |
| 5-ALA-n-hexanoicamide | (100) | 0 | 45 | 70 | 95 |
| | (500) | 0 | 45 | 75 | 95 |
| 5-ALA-n-nonanoicamide | (100) | 0 | 45 | 70 | 85 |
| | (500) | 0 | 45 | 60 | 80 |

TABLE 5-continued

| Sample compound | (Concentration (ppm)) | Amount added of NaCl per weight of soil (% by weight) | | | |
|---|---|---|---|---|---|
| | | 0 | 1.0 | 1.25 | 1.5 |
| Hemin | (100) | 0 | 45 | 70 | 95 |
| | (500) | 0 | 45 | 75 | 95 |
| 5-ALA hydrochloride | (100) | 0 | 40 | 50 | 75 |
| | (500) | 0 | 30 | 40 | 50 |

The results in Table 5 show that 5-ALA, esters of 5-ALA, N-acyl-5-aminolevulinic acids and hemin improve plant salt-tolerance.

Generally, as temperature increases, the salt damage to a plant also increases. In this example, the plants were cultivated in a glass hothouse in summer. However, even under such severe conditions, the active ingredients in the method according to the present invention clearly improved plant salt-tolerance.

Example 6 and Comparative Examples 12 and 13

A porcelain pot (inner diameter: 12 cm) having no drainage hole was filled with 600 g of soil of cultivated land. Sodium chloride corresponding to 0%, 0.5%, 1.0%, 1.5% or 2% by weight per the soil weight was dissolved in 50 ml of water, and then the solution obtained was dropwise added to the soil. Separately, young cotton plants which had been cultivated in a green house in a usual manner and had grown so that the first true leaf was revealed carefully pulled out. After washing the young plants with water, they were immersed in a 5-ALA solution (Example 6), a gibberellin solution (Comparative Example 12) or a benzyladenine solution (Comparative Example 13) shown in Table 6 for 36 hours. After the immersion, the young plants were washed and then transplanted in the above-described pot (November 11th).

After the usual cultivation, visual observation was done on the 18th day (November 29th). The results were evaluated in the same manner as in Example 1. The results are shown in Table 6 below.

TABLE 6

| | Sample compound | (Concentration (ppm)) | Amount added of NaCl per weight of soil (% by weight) | | | | |
|---|---|---|---|---|---|---|---|
| | | | 0 | 0.5 | 1.0 | 1.5 | 2 |
| Untreated | | | 0 | 1 to 2 | 4 | 5 | 5 |
| Example 6 | 5-ALA hydrochloride | (0.1) | 0 | 1 to 2 | 4 | 4 to 5 | 5 |
| | | (0.3) | 0 | 1 to 2 | 4 | 4 | 5 |
| | | (1) | 0 | 1 | 2 | 3 | 3 |
| | | (3) | 0 | 0 to 1 | 1 to 2 | 2 to 3 | 3 |
| | | (10) | 0 | 0 to 1 | 4 | 4 to 5 | 5 |
| Comparative Example 12 | Gibberellin (GA$_3$) | (0.01) | 0 | 1 to 2 | 4 | 5 | 5 |
| | | (0.03) | 0 | 1 to 2 | 4 | 5 | 5 |
| | | (0.1) | 0 | 1 to 2 | 4 to 5 | 5 | 5 |
| | | (0.3) | 0 | 1 to 2 | 4 | 5 | 5 |
| | | (1) | 0 | 1 to 2 | 4 | 5 | 5 |
| Comparative Example 13 | Benzyladenine (BA) | (0.03) | 0 | 1 to 2 | 4 | 5 | 5 |
| | | (0.1) | 0 | 1 to 2 | 4 | 5 | 5 |
| | | (0.3) | 0 | 1 to 2 | 4 | 5 | 5 |
| | | (1) | 0 | 1 to 2 | 4 to 5 | 5 | 5 |
| | | (3) | 0 | 2 | 4 to 5 | 5 | 5 |

The results in Table 6 show that, if plants are transplanted after a 5-ALA immersion treatment, the salt-tolerance thereof can be improved. On the other hand, in Comparative Examples, the salt-tolerance cannot be improved, and salt damage is promoted at a high salinity.

While the invention has been described in detail and with reference to specific embodiments thereof, it will be apparent to one skilled in the art that various changes and modifications can be made therein without departing from the spirit and scope thereof.

What is claimed is:

1. A method for improving plant salt-tolerance, which comprises treating a plant with an active ingredient, in a salt-tolerance improving amount or concentration, comprising at least one compound selected from the group consisting of 5-aminolevulinic acid, a derivative of 5-aminolevulinic acid, a salt of 5-aminolevulinic acid, a salt of derivatives of 5-aminolevulinic acid, and hemins.

2. The method as claimed in claim 1, wherein the salt of 5-aminolevulinic acid or the salt of derivatives of 5-aminolevulinic acid is at least one selected from the group consisting of hydrochloride, phosphate, nitrate, sulfate, acetate, propionate, butyrate, valerate, citrate, fumarate, maleate, malate, sodium salt, potassium salt and calcium salt.

3. The method as claimed in claim 1, wherein the derivative of 5-aminolevulinic acid is an ester of 5-aminolevulinic acid or N-acyl-5-aminolevulinic acid.

4. The method as claimed in claim 3, wherein the ester of 5-aminolevulinic acid is an ester of 5-aminolevulinic acid and a group selected from the group consisting of a methyl group, an ethyl group, an isopropyl group, an n-hexyl group, a cyclohexyl group, an n-heptyl group, an n-octyl group, an n-nonyl group, an n-dodecyl group, an n-hexadecyl group, a benzyl group, a phenethyl group, a 3-phenylpropyl group, a hydroxyethyl group, and an ethoxyethyl group.

5. The method as claimed in claim 3, wherein the N-acyl-5-aminolevulinic acid is 5-aminolevulinic acid acylated with an acyl group selected from the group consisting of an acetyl group, an n-pentanoyl group, an n-hexanoyl group, an n-nonanoyl group, a benzoyl group and a benzyloxycarbonyl group.

6. The method as claimed in claim 1, wherein the hemins are selected from the group consisting of heme, hemin, hematin, hemochrome, hemoglobin and blood powder.

7. The method as claimed in claim 1, wherein the active ingredient is mixed with at least one selected from the following: agents for regulating plant growth, saccharides, amino acids, organic acids, alcohols, vitamins and minerals.

8. The method as claimed in claim 1, wherein the plant is cultivated in soil having an electric conductivity of at least 0.5 milimho/cm in a soil solution at a ratio by weight of dry soil to water of 1:5.

9. The method as claimed in claim 1, wherein the plant is cultivated with irrigation water having a salt concentration of at least 300 ppm in water.

10. The method as claimed in claim 1, wherein the plant is treated by a foliage treatment with a solution containing the active ingredient at a concentration of 1 µmol/l to 15 mmol/l in an amount of 1 to 1,000 l per 10 ares of the ground.

11. The method as claimed in claim 1, wherein the plant is treated by a hydroponic treatment with a solution containing the active ingredient at a concentration of 6 nmol/l to 300 µmol/l.

12. The method as claimed in claim 1, wherein the plant is treated by applying a soil treatment in which the active ingredient is in an amount of 3 mmol to 5 mol per 10 ares of the soil.

13. The method as claimed in claim 1, wherein the plant is selected from the group consisting of cotton, asparagus, barley, wheat, corn, beet, tomato, fig, date palm, salt grass, Bermuda grass, radish, cabbage, Chinese cabbage, cucumber, eggplant, melon, rice, soybean, red clover, safflower and sunflower.

14. A method for causing recovery of a salt-damaged plant, comprising administering to a salt-damaged plant an active ingredient, in a salt-tolerance improving amount or concentration, comprising at least one compound selected from the group consisting of 5-aminolevulinic acid, a derivative of 5-aminolevulinic acid, a salt of 5-aminolevulinic acid, a salt of derivatives of 5-aminolevulinic acid, and hemins.

* * * * *